United States Patent [19]

Glassman et al.

[11] 4,320,722
[45] Mar. 23, 1982

[54] LIVESTOCK SPLINT

[75] Inventors: Stephen M. Glassman; James D. Kice; Paul A. Ryding, all of Wichita, Kans.

[73] Assignee: KRG, Inc., Wichita, Kans.

[21] Appl. No.: 149,269

[22] Filed: May 12, 1980

[51] Int. Cl.³ .......................... A61F 5/04; A01K 29/00
[52] U.S. Cl. ...................................... 119/96; 119/127; 128/85
[58] Field of Search .................... 119/96, 127; 128/82, 128/85, 87 R, 89 R, 90, 92 R; 54/82

[56] References Cited

U.S. PATENT DOCUMENTS 3,032,033  5/1962  Ramirez .............................. 128/90
3,470,873 10/1969  Walker et al. ................ 128/89 R X
3,881,472  5/1975  Lee .................................. 119/96 X

FOREIGN PATENT DOCUMENTS 2308351 11/1976  France ............................... 128/87 R
542305   4/1956  Italy ................................... 128/87 R
950098   2/1964  United Kingdom ............. 128/87 R Primary Examiner—Gene Mancene
Assistant Examiner—Robert P. Swiatek
Attorney, Agent, or Firm—John H. Widdowson

[57] ABSTRACT

An animal brace having a shell member; a truss support embedded in the shell; a plate attaching to the truss support; a core connecting to the plate; and a toe wedge having a structured portion of the core embedded therein.

12 Claims, 7 Drawing Figures

LIVESTOCK SPLINT

BACKGROUND OF THE INVENTION

1. Field of the Invention

This invention is related to an animal brace. More specifically this invention provides an equine animal splint which may be placed on the front or the rear leg of the animal.

2. Description of the Prior Art

Historically, veterinarians and laymen have designed and constructed a variety of braces and fixation devices. Two common problems have been consistent with these devices. First, the units are too heavy and cumbersome. Second, they fail to adequately support the injured leg, primarily due to the difficulty in applying the device without other support items.

U.S. Pat. No. 4,029,090 describes an apparatus designed to be used with casting material with the intent of adding to the support of the leg. U.S. Pat. No. 4,044,760 shows a small plastic device with the intended purpose of supporting the flexor tendons. U.S. Pat. No. 4,099,525 describes a device using cast material in an attempt to stretch contracted tendons.

SUMMARY OF THE INVENTION

This invention accomplishes its desired objects by providing an animal leg brace which fits behind the leg of the animal having a shell member for partially encasing the leg of the animal; a truss support means embedded in the shell for supporting the shell as it partially surrounds the leg of the animal; a plate means attaching to the truss support member; and a core means connecting to the plate means. A toe wedge means for supporting the hoof of the animal has a structural portion of the core means embedded therein.

It is an object of the invention to provide a leg brace which is easily assembled and economical to manufacture.

Still further objects of the invention reside in the provision of an animal brace which can be easily attached to the leg of an animal.

These together with the various ancillary objects and features will become apparent as the following description proceeds, are attained by this animal brace, preferred embodiments being shown in the accompanying drawings, by way of example only, wherein:

DETAILED DESCRIPTION OF THE DRAWINGS

Figure 1:
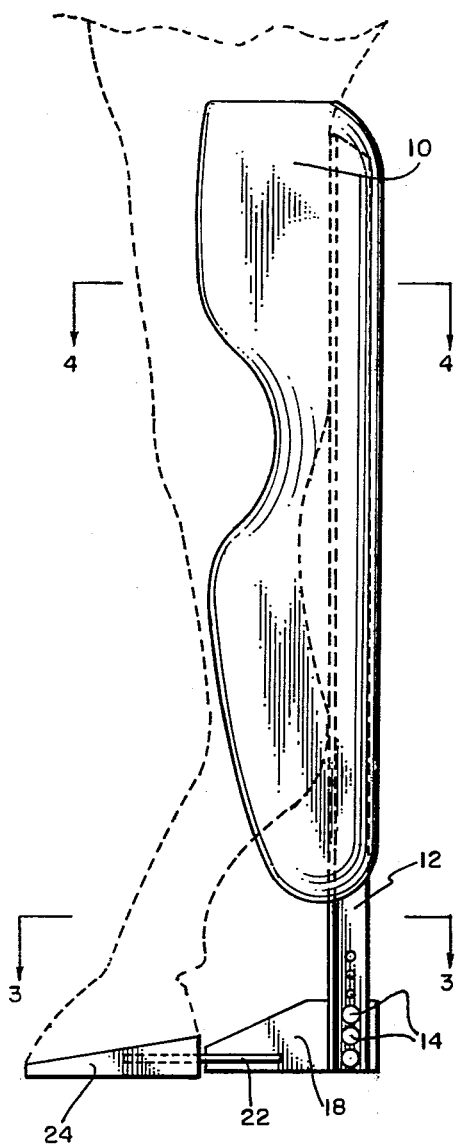
FIG. 1 is a side elevational view of the animal leg brace with an animal's front leg represented by dotted lines.
Figure 2:
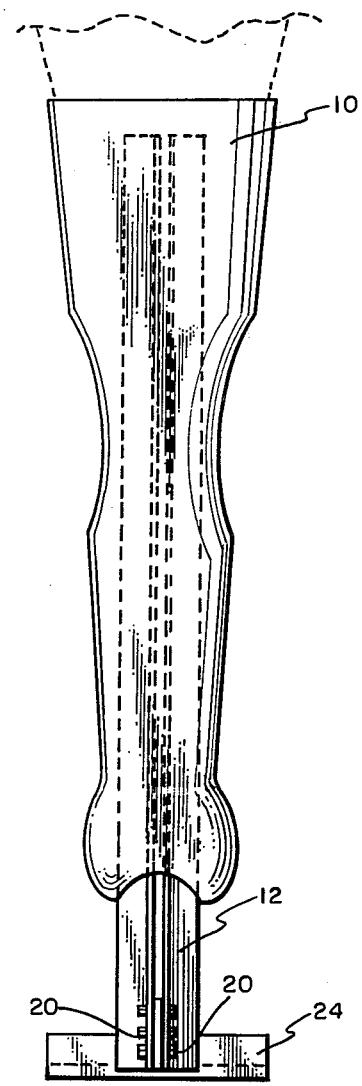
FIG. 2 is a rear elevational view of the animal leg brace.
Figure 3:
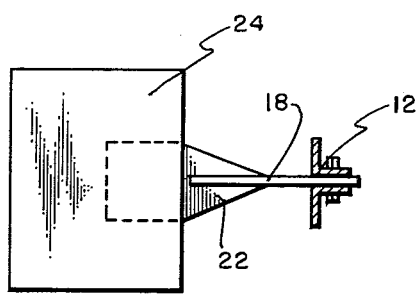
FIG. 3 is a horizontal sectional view taken along the plane of line 3—3 in FIG. 1.
Figure 4:
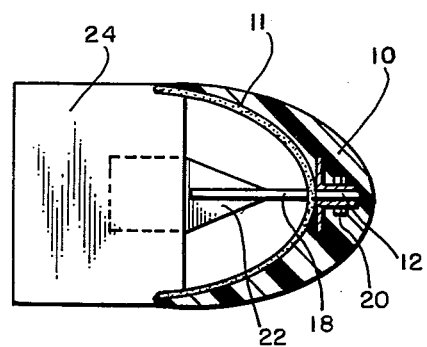
FIG. 4 is a horizontal sectional view taken along the plane of line 4—4 in FIG. 1.

Referring in detail now to the drawings, wherein like reference numerals designate similar parts throughout the various views, a fiberglass reinforced plastic shell 10 with a soft, resilient liner 11 partially encases the leg of an animal and has essentially the entire length of a T-shaped aluminum truss member 12, including apertures 14, embedded therein for supporting the shell 10 as it partially surrounds the leg of the animal. Truss 12 has a sinusoidal shaped bar member 16 connected thereto in order to strengthen and reinforce the embedment of the truss 12 in the shell 10. A vertical plate 18 is provided having apertures (not readily seen in the drawings) registering with the truss apertures 14 for vertically adjusting the plate 18 by inserting fastener 20 through one of the plate apertures and one of the truss apertures 14 for securing the plate 18 to the truss 12.

Figure 5:
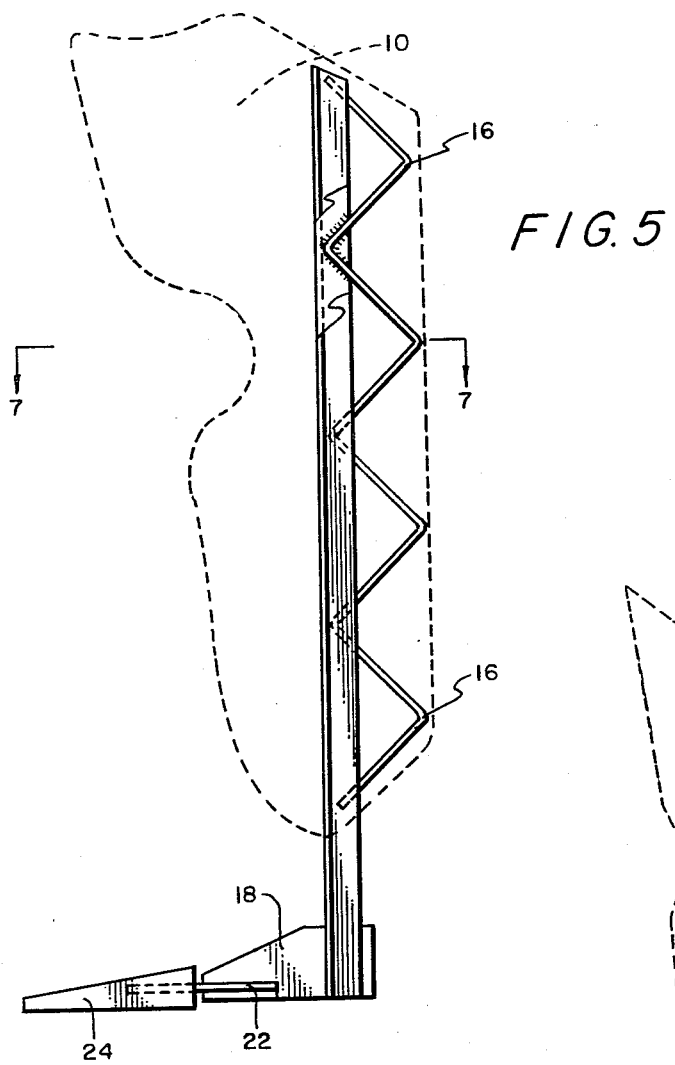
FIG. 5 is a side elevational view of another embodiment of the animal leg brace with an animal's rear leg represented by dotted lines.
Figure 6:
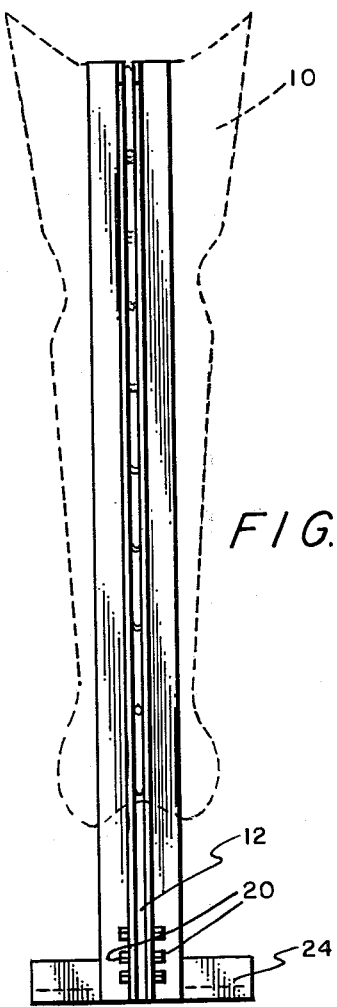
FIG. 6 is a rear elevational view of the brace of FIG. 5.
Figure 7:
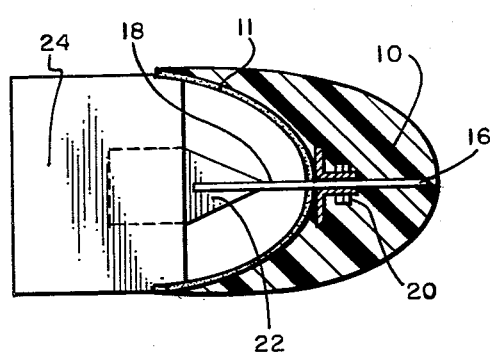
FIG. 7 is a horizontal sectional view taken along the plane of line 7—7 in FIG. 5.

A metallic, horizontal core means 22 connects to the plate 18, and has a plastic (urethane or neoprene) toe wedge means 24 molded around a part thereof so that when the hoof of the animal is glued or nailed to the wedge means 24, the excess plastic wedge 24 surrounding the outside of the hoof can be trimmed away. The wedge means 24 is triangular in vertical cross section as seen in FIGS. 1 and 5.

With continuing reference to the drawings, and in particular FIG. 1, for operation of the invention, the leg of an animal (represented by dotted lines in FIG. 1) is placed in the shell 10 with the hoof situated on the toe wedge 24. The hoof is attached to the toe wedge 10 by either glue or nails, and the excess wedge material surrounding the hoof may be trimmed away. In a preferred embodiment of the drawings, the leg brace in FIG. 1 is used for a front leg and the leg brace in FIG. 5 is used for a rear leg.

While the present invention has been described herein with reference to particular embodiments thereof, a latitude of modification, various changes and substitutes are intended in the foregoing disclosure, and it will be appreciated that in some instances some features of the invention will be employed without a corresponding use of other features without departing from the scope of the invention as set forth.

We claim:

1. An animal leg brace or splint which fits behind the leg of the animal comprising: a shell member for partially encasing the leg of the animal; a truss support means embedded in said shell for supporting the shell as it partially surrounds the leg of the animal; a plate means attached to said truss support means; a core means connected to said plate means; and a toe wedge means for supporting the hoof of the animal and having a structural portion of said core means embedded therein; said toe wedge means is constructed of a plastic means which has been molded around part of said core means so that when the hoof of the animal is glued or nailed to the wedge means, the excess plastic means surrounding the outside of the hoof is capable of being trimmed away, said toe wedge means is essentially triangular in a vertical cross section, said truss means having a plurality of truss apertures, said plate means is vertically disposed with respect to a horizontal plane and includes a structure defining a plurality of plate apertures registering with said truss apertures for vertically adjusting said plate means by inserting a fastener means through one of the plate apertures and one of the truss apertures for securing said plate means to said truss means.

2. The brace of claim 1 wherein said core means is metallic and horizontally disposed with respect to said plate means.

3. The brace of claim 2 wherein said truss support means comprises a generally sinusoidal shaped bar member which strengthens and reinforces the embedment of the truss means in said shell.

4. The brace of claim 3 wherein essentially the entire length of said truss means including the sinusoidal bar member is embedded in the shell.

5. The brace of claim 4 additionally comprising a soft, resilient means lining the inside of said shell member to protect the leg of the animal.

6. An animal leg brace or splint which fits behind the leg of the animal comprising: a shell member having a back and for partially encasing the leg of the animal; a truss support means generally traversely embedded in and across the entire back of said shell for supporting the shell as it partially surrounds the leg of the animal; a plate means adjustably attached to said truss support means and extending substantially perpendicular thereto; a core means integrally bound to said plate means; and a toe wedge means for supporting the hoof of the animal and having a structural portion of said core means embedded therein.

7. The brace of claim 6 wherein said toe wedge means is constructed of a plastic means which has been molded around part of said core means so that when the hoof of the animal is glued or nailed to the wedge means, the excess plastic means surrounding the outside of the hoof is capable of being trimmed away.

8. The brace of claim 2 wherein said toe wedge means is essentially triangular in a vertical cross section, said truss means having a plurality of truss apertures.

9. The brace of claim 8 wherein said core means is metallic and horizontally disposed with respect to said plate means.

10. The brace of claim 9 wherein said truss support means comprises a generally sinusoidal shaped bar member which strenthens and reinforces the embedment of the truss means in said shell.

11. The brace of claim 10 wherein essentially the entire length of said truss means including the sinusoidal bar member is embedded in the shell.

12. The brace of claim 11 additionally comprising a soft, resilient means lining the inside of said shell member.

* * * * *